United States Patent [19]

Bradshaw et al.

[11] Patent Number: 5,385,833
[45] Date of Patent: Jan. 31, 1995

[54] *PSEUDOMONAS SP.* ATCC NO. 49794 ALCOHOL DEHYDROGENASE

[75] Inventors: Curt W. Bradshaw, San Diego; Chi-Huey Wong, Rancho Santa Fe; Gwo-Jenn Shen, Carlsbad, all of Calif.

[73] Assignee: The Scripps Research Institute, La Jolla, Calif.

[21] Appl. No.: 841,718

[22] Filed: Feb. 26, 1992

[51] Int. Cl.$^6$ ............ C12P 7/02; C12P 7/00; C12N 1/20; C12R 1/38
[52] U.S. Cl. ............ 435/156; 435/155; 435/157; 435/160; 435/161; 435/132; 435/148; 435/253.3; 435/280; 435/874
[58] Field of Search ............ 435/280, 132, 148, 155, 435/253.3, 874, 156, 157, 160, 161, 155, 253.3, 874

[56] References Cited

PUBLICATIONS

Hou et al., *Eur. J. Biochem*, 119, 359–364 (1981).
Shaw et al., *Eur. J. Biochem*, 191, 705–714 (1990).
Bradshaw et al., *J. Org. Chem.*, 57, 1526–1532 (1992).
Bradshaw et al., *Bioorganic Chemistry*, 19, 398–417 (1991).
Shen et al., *J. Chem. Soc.*, Chem. Commun., No. 9, 677–679, (1990).
Hummel et al., *Eur. J. Biochem.*, 184:1 (1989).
Whitesides et al., *Angew. Chem. Int. Ed. Engl.*, 24:617 (1985).
Keinan et al., *J. Am. Chem. Soc.*, 108:162 (1986).
Keinan et al., *J. Am. Chem. Soc.*, 108:3474 (1986).
Drueckhammer et al., *Enzyme Microb. Technol.*, 9:564 (1987).
Drueckhammer et al., *J. Org. Chem.*, 53:1607 (1988).
Prelog, *Pure Appl. Chem.*, 9:119 (1964).
Hummel, *Biotech, News Lett.*, 12:403–408 (1990).
Hummel, *Appl. Microbiol. Biotechnol.*, 34:15–19 (1990).
Dale et al., *J. Org. Chem.*, 34:2543 (1969).
Peters et al., *J. Org. Chem.*, 33:4245 (1968).
Ziffer et al., *J. Org. Chem.*, 48:3017 (1873).

*Primary Examiner*—David M. Naff
*Assistant Examiner*—Maria Luisa Osoteo
*Attorney, Agent, or Firm*—Welsh & Katz, Ltd.

[57] ABSTRACT

The present invention provides a substantially pure culture of *Pseudomonas sp.* strain PED having the ATCC designation 49794. Processes for making R-configured alcohols and for transferring a hydride ion from an R-configured alcohol to the pro-R face of NAD using PED alcohol dehydrogenase isolated and purified from *Pseudomonas sp.* strain PED are also provided.

12 Claims, No Drawings

PSEUDOMONAS SP. ATCC NO. 49794 ALCOHOL DEHYDROGENASE

DESCRIPTION

1. Technical Field of the Invention

The present invention relates to a substantially pure culture of *Pseudomonas sp.* strain PED having the ATCC designation 49794, and processes for forming R-configured alcohols and transferring a hydride ion from an R-configured alcohol to the pro-R face of NAD using an alcohol dehydrogenase enzyme preparation isolated from that microorganism.

2. Background of the Invention

Alcohol dehydrogenases are well known enzymes that catalyze the interconversion of carbonyl compounds and alcohols. See. e.g., Hummel et al., *Eur. J. Biochem.*, 184: 1 (1989), Whitesides et al., *Angew. Chem. Int. Ed. Engl.*, 24: 617 (1985), Lemiere, "Enzymes as Catalysts in Organic Synthesis", Schneider, M. P. ed., D. Reidel Publishing, pp 19-34 (1986), Jones et al., in "Applications of Biochemical Systems in Organic Synthesis" Jones, J. B.; Sih, C. J.; Perlman, D. eds., John Wiley and Sons, New York, pp 248-376 (1976), Jones, "Mechanisms of Enzymatic reactions: Stereochemistry" Frey, P. A. ed., Elsevier Science, 3-14 (1986); Jones, J. B. "Enzymes in Organic Synthesis" Ciba Foundation Symposium III, Pitman, London, pp 3-14 (1985), Keinan et al., *J. Am. Chem. Soc.*, 108: 162 (1986), Keinan et al., *J. Am. Chem. Soc.*, 108: 3474 (1986), Drueckhammer et al., *Enzyme Microb. Technol.*, 9: 564 (1987), Drueckhammer et al., *J. Org. Chem.*, 53: 1607 (1988).

The most extensively used and studied alcohol dehydrogenases have been obtained from horse liver, yeast and the bacteria *Thermoanaerobium brokii*.

Alcohol dehydrogenase action involves the transfer of a hydride between a substrate (an alcohol or an aldehyde or ketone; i.e., a carbonyl substrate) and a cofactor, which serves as a hydride acceptor or donor. Typically, the cofactor for alcohol dehydrogenase is nicotinamide adenine dinucleotide (NAD), reduced nicotinamide adenine dinucleotide (NADH), nicotinamide adenine dinucleotide phosphate (NADP), or reduced nicotinamide adenine dinucleotide phosphate (NADPH).

NAD and NADP are major electron ($e^-$) acceptors in the oxidation of molecules. The reactive part of NAD or NADP is the nicotinamide ring.

In the oxidation of a substrate molecule such as an alcohol, that nicotinamide ring accepts a hydride ion and is reduced. As used herein, the phrase "hydride ion" means $H^-$ (a proton associated with two electrons), deuteride ($D^-$) (a deuterium ion associated with two electrons) or tritide ($T^-$) (a tritium ion associated with two electrons). These three isotopic hydride ions can also be referred to as $^1H^-$, $^2H^-$ and $^3H^-$.

Any of those hydride ions can be used to reduce NAD or NADP. The reduced forms of NAD and NADP are referred to herein as NADH and NADPH, respectively. By way of example, the structure of NADH is shown below.

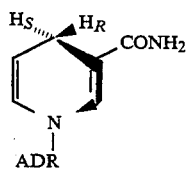

The two depicted hydrogens bonded to the nicotinamide ring of NADH are designated $H_S$ and $H_R$. Those designations are used to indicate the spatial orientation of those hydrogens. The $H_S$ hydrogen has the S configuration and the $H_R$ hydrogen has the R configuration.

Where NADH or NADPH serves as a hydride donor for alcohol dehydrogenase activity, the hydride can be either the $H_S$ or the $H_R$. Conversely, where NAD or NADP serves as the hydride acceptor for alcohol dehydrogenase activity, the added hydride can be either the $H_S$ or the $H_R$.

Where the added or donated hydride is $H_R$, the alcohol dehydrogenase is said to act on the pro-R face of the cofactor. Where the added or donated hydride is $H_S$, the alcohol dehydrogenase is said to act on the pro-S face of the cofactor.

The carbonyl substrates for alcohol dehydrogenase action exist in two potentially diastereotopic forms, where the side chains attached to the carbonyl carbon are different. Two such arrangements are shown for a carbonyl substrate in formulae II and III, below, where the side chain groups X and Y are of different size (i.e. molecular weight) with X>Y.

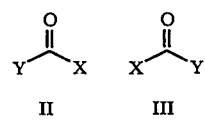

If the three groups by standard sequence rules have the order X>Y, that face in which the two groups are placed in a plane and arranged in a clockwise manner (formula II, above) is referred to as the Re face. That face in which the two groups are similarly placed in a plane and arranged in a counterclockwise manner (formula III, above) is referred to as the Si face.

Alcohol dehydrogenases can act by reducing a carbonyl substrate by adding a hydride ion to either the Re or the Si face of that carbonyl. Alcohol dehydrogenases that add a hydride ion to the Re face are said to follow Prelog's Rule. Alcohol dehydrogenases that add a hydride ion to the Si face are said to follow Anti-Prelog's Rule. Prelog, *Pure Appl. Chem.*, 9: 119 (1964).

Alcohol dehydrogenases that follow Prelog's Rule produce alcohols wherein the carbon atom bearing the formed hydroxyl group has the S configuration. Alcohol dehydrogenases that follow Anti-Prelog's Rule produce alcohols wherein the carbon atom bearing the formed hydroxyl group has the R configuration.

In view of the known cofactor and substrate stereoconfigurations, it can be seen that alcohol dehydrogenases can work in one of four ways. Those four possible mechanisms are illustrated below in Scheme 1 and are designated $E_1$, $E_2$, $E_3$ and $E_4$.

Scheme 1

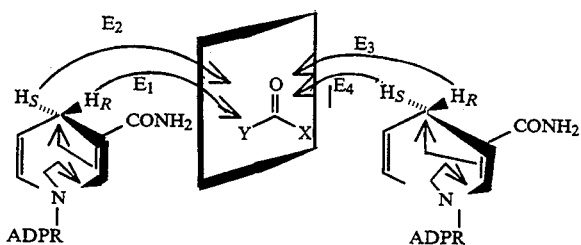

The $E_1$ mechanism is characterized by specificity for the pro-R hydrogen of the cofactor and addition of a hydride ion to the Si face of a carbonyl substrate. The $E_2$ mechanism is characterized by specificity for the pro-S hydrogen of the cofactor and addition of a hydride ion to the Si face of a carbonyl substrate. The $E_3$ mechanism is characterized by specificity for the pro-R hydrogen of the cofactor and addition of a hydride ion to the Re face of a carbonyl substrate. The $E_4$ mechanism is characterized by specificity for the pro-S hydrogen of the cofactor and addition of a hydride ion to the Re face of a carbonyl substrate.

The previously described alcohol dehydrogenases from horse liver, yeast and *Thermoanaerobium brokii* are all characterized as operating via the $E_3$ mechanism (i.e., they catalyze the transfer of a hydride ion from the pro-R face of the cofactor to the Re face of a carbonyl substrate to produce an alcohol having the S configuration. Prelog, *Pure Appl. Chem.*, 9: 119 (1964).

An alcohol dehydrogenase has been isolated from *Mucor javanicus* and found to operate via the $E_2$ mechanism.

Recently, an alcohol dehydrogenase enzyme has been isolated from *Lactobacillus kefir*. Hummel, *Biotech. News Lett.*, 12: 403–408 (1990); Hummel, *Appl. Microbiol. Biotechnol.*, 34: 15–19 (1990). That enzyme was found to operate via the $E_1$ mechanism. A second alcohol dehydrogenase that uses the $E_1$ mechanism has recently been isolated from *Pseudomonas sp.* strain SBD6.

Alcohol dehydrogenases can be further characterized by their specificity for certain cofactors and their ability to act on substrates of varying structural complexity. In this regard, alcohol dehydrogenases can, typically, use either but not both of NAD(H) or NADP(H) as cofactor.

The alcohol dehydrogenases from *Pseudomonas sp.* strain SBD6, horse liver, yeast and *Thermoanaerobium brokii* further require that the carbonyl or hydroxyl group of the substrate be adjacent to a methyl group. Although the alcohol dehydrogenase from *Lactobacillus kefir* can use such methyl-substituted substrates, that enzyme is not limited to such substrates. Rather, that enzyme can use substrates having aromatic, aliphatic and cyclic side chains. In addition, that enzyme can use certain silicon-containing carbonyl substrates. Hummel, *Appl. Microbiol. Biotechnol.*, 34: 15 (1990).

In view of the foregoing, it can be seen that there is no predictable relationship between carbonyl substrate structural specificity and hydride transfer mechanism for alcohol dehydrogenases.

BRIEF SUMMARY OF THE INVENTION

The present invention relates to an alcohol dehydrogenase preparation isolated from *Pseudomonas sp.* strain PED. The alcohol dehydrogenase of the present invention is similar to the enzyme from *Pseudomonas sp.* strain SBD6 in following Anti-Prelog's Rule but is unlike the enzyme from *Pseudomonas sp.* strain SBD6 in that the alcohol dehydrogenase of the present invention accepts a wide range of carbonyl substrates.

In one aspect, the present invention relates to a substantially pure culture of the microorganism *Pseudomonas sp.* strain PED having the ATCC designation 49794. An alcohol dehydrogenase preparation from this strain is referred to herein as PED alcohol dehydrogenase.

In another aspect, the present invention relates to a process of making an R-configured alcohol comprising the steps of:

(a) forming a reaction mixture by admixing in a liquid medium (i) NADH, (ii) a catalytic amount of a PED alcohol dehydrogenase preparation and (iii) a carbonyl substrate of the formula I, below:

$$R\text{—}CO\text{—}R^1 \qquad\qquad I$$

wherein R is hydrogen, $C_1\text{–}C_6$ alkyl, $C_1\text{–}C_6$ haloalkyl, $C_1\text{–}C_6$ acyl, $C_1\text{–}C_6$ alkoxy carbonyl, $C_1\text{–}C_6$ alkene and $C_1\text{–}C_6$ azaalkyl;

$R^1$ is selected from the group consisting of phenyl, benzoyl, pyridyl, $C_1\text{–}C_3$ alkylenephenyl, $C_2\text{–}C_3$ oxaalkylenephenyl, $C_1\text{–}C_6$ alkoxy carbonyl, $C_1\text{–}C_6$ alkenyl, $C_1\text{–}C_6$ alkyl, $C_1\text{–}C_6$ haloalkyl, $C_1\text{–}C_6$ oxoalkyl, $C_1\text{–}C_6$ halo oxoalkyl, $C_1\text{–}C_3$ alkyl $C_1\text{–}C_3$ alkylenecarboxylate, $C_2\text{–}C_3$ alkynyl, $C_1\text{–}C_6$ hydroxy alkyl, $C_1\text{–}C_6$ oxoalkyl and $C_1\text{–}C_6$ thiaalkyl, or R and $R^1$ together form a 5–7-membered ring that is free from unsaturation except for the carbonyl of formula I; and said carbonyl substrate has an overall chain length of three to about nine carbon atoms; and (b) maintaining the reaction mixture under biological reaction conditions and for a time period sufficient to reduce the carbonyl substrate and form the R-configured alcohol.

In a preferred embodiment, the process further comprises the step of recovering the formed R-configured alcohol.

The PED alcohol dehydrogenase used in the process is a preparation isolated from *Pseudomonas sp.* strain PED having the ATCC designation 49794.

In another preferred embodiment, the liquid medium contains a water immiscible, non-reactive organic solvent for the carbonyl substrate.

In preferred practice, R is $C_1\text{–}C_6$ alkyl, and $R^1$ is phenyl, benzoyl, $C_1\text{–}C_6$ alkyl, $C_1\text{–}C_6$ oxoalkyl, $C_1\text{–}C_6$ halooxoalkyl, and $C_1\text{–}C_3$ alkyl $C_1\text{–}C_3$ alkylenecarboxylate. Most preferred, R is methyl.

In another aspect, the present invention provides a process of forming an R-configured alcohol with the regeneration of NADH, which process comprises the steps of (a) forming a reaction mixture by admixing on a liquid medium (i) a catalytic amount of NAD, (ii) a catalytic amount of a PED alcohol dehydrogenase preparation, (iii) a cofactor alcohol substrate and (iv) a carbonyl substrate of the formula I, above; and (b) maintaining said reaction mixture under biological reaction conditions and for a time period sufficient to reduce said carbonyl substrate and form said R-configured alcohol.

In a preferred embodiment, the cofactor alcohol substrate is 2-propanol.

In another aspect, the present invention relates to a process of transferring a hydride ion to the pro-R face of NAD comprising the steps of (a) forming a reaction mixture by admixing in a liquid medium (i) said NAD, (ii) a catalytic amount of PED alcohol dehydrogenase and (iii) an R-configured alcohol of the formula Ia, below:

   Ia wherein R and $R^1$ and the chain length of the R-configured alcohol are as defined before, $R^2$ is hydrogen, deuterium or tritium; and (b) maintaining the reaction mixture under biological reaction conditions and for a time period sufficient to oxidize the R-configured alcohol and transfer the hydride ion from the R-configured alcohol to NAD and form NADH.

DETAILED DESCRIPTION OF THE INVENTION

A. Compositions

1. Culture of *Pseudomonas sp.* strain PED

In one aspect, the present invention relates to a substantially pure culture of the microorganism *Pseudomonas sp.* strain PED. A substantially pure culture of the microorganism is substantially free of contamination by other microorganisms. That culture was deposited in accordance with the Budapest Treaty with the American Type Culture Collection (ATCC), 12301 Parklawn Drive, Rockville, Md. 20852, was received by them on Aug. 15, 1991 and assigned the designation ATCC 49794.

The above deposit is made for a term of at least thirty (30) years after the date of deposit and shall be maintained at least five (5) years after the most recent request for a sample.

The *Pseudomonas sp.* strain PED of the present invention was isolated and purified using standard techniques well known in the art (See Example 1 hereinafter).

Briefly, microorganisms from garden soil were enriched in a medium containing (±)-1-phenyl-1,2-ethanediol as the sole carbon and energy source. Enrichment was carried out at 30° C. with shaking (250 rpm) in 125 ml serum bottles containing 70 ml of the screening medium and 0.1 g of garden soil as the source of microorganisms. Those enrichments that showed growth were plated onto agar plates.

Single colonies were transferred into serum bottles containing the same screening medium, and growing cultures were plated on LB agar plates (10 g tryptone, 5 g yeast extract, 0.5 g NaCl, and 15 g agar per liter distilled water, pH 7.0) to ensure homogeneity of the colonies.

One bacterial strain exhibiting prodigious growth was chosen for further study. That strain was morphologically and physiologically characterized according to standard procedures well known in the art.

The microorganisms were observed to be obligate aerobe short rods, 1–1.5 $\mu M$ in diameter. The gram negative colonies were found to have a cream color with a smooth edge and surface.

The isolated microorganisms were further found to be positive for arginine dihydrolase, OF xylose, OF aerobic dextrose, citrate utilization and oxidase activity and negative for OF anaerobic dextrose, $H_2S$ formation, indole formation, and urease.

On the basis of those morphological and physiological characteristics, the microorganism was identified as belonging to *Pseudomonas sp.*, Bergey's Manual of Systematic Bacteriology, Krieg, N. R. ed; Williams and Wilkins Co., Baltimore, 1984. The isolated and purified *Pseudomonas sp.* strain contemplated by the present invention is designated PED.

The isolated and purified alcohol dehydrogenase enzyme of the present invention, designated PED alcohol dehydrogenase, is characterized as (1) following Anti-Prelog's Rule in hydride addition and (2) having specificity for the pro-R hydride face of oxidized and reduced forms nicotinamide adenine dinucleotide (NAD and NADH, respectively).

PED alcohol dehydrogenase is isolated and purified from cultures of *Pseudomonas sp.* strain PED using standard techniques well known in the art.

Briefly, cell cultures of *Pseudomonas sp.* strain PED were obtained during the late exponential growth phase were harvested by centrifugation at 8000 rpm for 20 minutes. The harvested cells were suspended in 87 ml 30 mM TRIS buffer, pH 7, containing 4 mM dithiothreitol (DTT) and ruptured in a SLM Aminco French Press (23,000 psi).

A cell extract was obtained as the supernatant after centrifugation at 15000 rpm for 75 minutes. Solid ammonium sulfate was added to the cell extract to a final concentration of 20–60 percent ammonium sulfate and the pellet was dialyzed for five hours versus 30 mM TRIS buffer, pH 7.5 containing 4 mM DTT (buffer A) and applied to a previously equilibrated DEAE-Sepharose CL6B column.

After the nonbinding components were eluted as determined by absorbance at 254 nm, a 0–200 mM ammonium sulfate gradient in buffer A was begun (total volume 1 L). The tubes containing NAD-dependent (±)-1-phenyl-1,2-ethanediol and 2-propanol oxidizing activity were collected, concentrated in an Amicon protein concentrator, and applied to an Ultragel AcA34 gel filtration column (5×125 cm).

The fractions containing activity were combined, concentrated, and applied to a 5 $cm^3$ $\beta$-NAD agarose affinity column (attached through N6 with an 8 carbon spacer). After washing the column, the enzyme was eluted with 10 mM NAD in buffer A.

The isolated PED alcohol dehydrogenase enzyme exhibited $K_m$ values of 525 $\mu M$ and 75 $\mu M$ for NAD and 2-propanol, respectively. The specific activity is 36 U/mg with respect to 2-propanol under saturating NAD conditions.

The kinetic mechanism of PED alcohol dehydrogenase activity was established with initial velocity patterns and product inhibition studies. Lineweaver-Burke plots of the initial velocity for the oxidation of 2-propanol at different constant concentrations of NAD were intersecting. Product inhibition studies for the oxidation of 2-propanol revealed noncompetitive inhibition with acetone and competitive inhibition with NADH versus NAD. These two products are both noncompetitive inhibitors of 2-propanol.

These results fulfill criteria for an ordered bi-bi mechanism where the binding order is NAD followed by 2-propanol. The release of products is acetone then the reduced cofactor. The amount of substrates used in these studies were from 0.2 to 2.5 times the $K_m$ concentrations.

Alcohol dehydrogenase PED can be used in its isolated and purified form. However, it is frequently more convenient and preferred to use that enzyme as an isolated, relatively crude cellular extract of the before-described bacterium as is described in Example 4B, hereinafter.

Alcohol dehydrogenase PED from *Pseudomonas sp.* PED ATCC No. 49794 utilized herein is referred to generally as an isolated preparation of that enzyme to encompass both the isolated, purified enzyme and the relatively crude enzyme preparation as obtained from the supernatant of broken, centrifuged cells. That preparation can be present in solid form such as a lyophilized product, or in liquid form in an aqueous medium.

The amount of an isolated preparation of the enzyme used in a process discussed hereinafter is a catalytic amount. As used herein, the phrase "catalytic amount" means that amount of PED alcohol dehydrogenase at least sufficient to catalyze, in a non-rate limiting manner, the conversion of that enzyme's substrate (e.g., a carbonyl substrate of formula I) to product (an R-configured alcohol).

The catalytic amount of PED alcohol dehydrogenase varies according to the nature and concentration of that enzyme's substrate as well as to reaction conditions such as temperature, time and pH value. Means for determining the catalytic amount for PED alcohol dehydrogenase of the present invention under preselected substrate concentrations and reaction conditions are well known to those of skill in the art. It is to be understood, however, that more than a catalytic amount can be used to speed the reaction, as where preparative amounts of a desired R-configured alcohol are desired.

Thus, for example, where the stereochemistry of a particular reaction is being studied, an enzyme preparation containing about 20 units of activity can be used with about 150 mg of NAD or NADH and an excess of alcohol or carbonyl substrate, respectively. Where a preparative amount of product is desired, it is convenient to use about one gram of a solid enzyme preparation with about five mmoles of substrate and 50 mg of NAD or NADH, as appropriate. A skilled worker can adjust the amounts of reagents as is well known to obtain a faster reaction or a higher yield of a desired product.

B. Processes

1. A process of forming an R-configured Alcohol

In another aspect, the present invention relates to a process of making an R-configured alcohol comprising the steps of:

(a) forming a reaction mixture by admixing in a liquid medium (i) NADH, (ii) a catalytic amount of a PED alcohol dehydrogenase preparation as discussed before and (iii) a carbonyl substrate of the formula I, below:

wherein R is hydrogen, $C_1-C_6$ alkyl, $C_1-C_6$ haloalkyl, $C_1-C_6$ acyl, $C_1-C_6$ alkoxy carbonyl, $C_1-C_6$ alkene and $C_1-C_6$ azaalkyl;

$R^1$ is selected from the group consisting of phenyl, benzoyl, pyridyl, $C_1-C_3$ alkylenephenyl, $C_2-C_3$ oxaalkylenephenyl, $C_1-C_6$ alkoxy carbonyl, $C_1-C_6$ alkenyl, $C_1-C_6$ alkyl, $C_1-C_6$ haloalkyl, $C_1-C_6$ oxoalkyl, $C_1-C_6$ halo oxoalkyl, $C_1-C_3$ alkyl $C_1-C_3$ alkylenecarboxylate, $C_2-C_3$ alkynyl, $C_1-C_6$ hydroxy alkyl, $C_1-C_6$ oxoalkyl and $C_1-C_6$ thiaalkyl, or R and $R^1$ together form a 5-7-membered ring that is free from unsaturation except for the carbonyl of formula I; and said carbonyl substrate has an overall chain length of three to about nine carbon atoms; and (b) maintaining the reaction mixture under biological reaction conditions and for a time period sufficient to reduce the carbonyl substrate and form the R-configured alcohol.

The process of forming an R-configured alcohol involves the transfer of a hydride ion from NADH to the carbonyl substrate. Thus, in addition to forming an R-configured alcohol, the process also forms NAD.

A water-immiscible, alcohol-, ketone- or aldehyde-free (non-reactive) organic solvent for the carbonyl substrate such as hexane, ethyl ether or benzene is also preferably present in the reaction mixture. That solvent provides a phase transfer medium for a carbonyl substrate and alcohol product (and vice versa) that has only minimal water-solubility, as compared to using a dispersed, but undissolved carbonyl reactant.

Exemplary $C_1-C_6$ alkyl groups include straight and branched chain as well as cyclic radicals such as methyl, ethyl, isopropyl, butyl, sec-butyl, cyclopropyl, cyclohexyl, and 2-hexyl. Exemplary $C_1-C_6$ alkenyl groups include straight and branched chain radicals such as vinyl, 1- or 2-propenyl, vinyl, 1-methylvinyl, 1-butenyl, 2-butenyl, and 2-methylpentenyl. Exemplary $C_2-C_3$ alkynyl groups include acetylenyl, and 1- and 2-propynyl radicals.

A haloalkyl group is an above alkyl group containing one or more halogens. Exemplary $C_1-C_6$ haloalkyl groups are chloroethyl, chloropropyl, trifluoromethyl, trifluoropropyl, 2-chlorohexyl and bromoethyl. A $C_1-C_2$ hydroxyalkyl group is similarly a before-described $C_1-C_2$ alkyl group that includes an hydroxyl group.

The presence of a $C_1-C_6$ acyl group in a carbonyl substrate of formula I provides an α-diketone. A $C_1-C_6$ acyl group is thus a $C_1-C_5$ alkyl group terminated by a carbonyl group that is bonded to the depicted carbonyl, and as such, the $C_1-C_5$ alkyl portion thereof can be a straight or branched chain alkyl group as discussed before.

The presence of an $C_1-C_6$ alkoxy carbonyl group provides an α-ketocarboxylic acid ester substrate in which the alcohol portion of the ester is formed from a $C_1-C_6$ alkyl alcohol. That alkyl portion of that alcohol is a before-described straight or branched chain $C_1-C_6$ alkyl group.

A $C_1-C_6$ aza-, thia- or oxaalkyl group is a before-described $C_1-C_6$ alkyl group, one or two of whose carbon atoms have been substituted for in the alkyl chain by a nitrogen, sulfur or oxygen atom, respectively. Exemplary groups include 3-aza-3-methylbutyl, 1-methyl-2-thiapropyl, 1-(α-oxapropyl)-2-oxabutyl and 1-(α-oxaethyl)-2-oxapropyl radicals.

A $C_1-C_3$ alkylenephenyl radical includes a phenyl group linked to one through three carbons, one of which carbons is linked to the carbonyl group of formula I. Exemplary $C_1-C_3$ alkylenephenyl groups include benzyl, phenethyl and 2-phenylpropyl radicals. A $C_2-C_3$ oxaalkylene phenyl radical has a carbon atom of the alkylene chain replaced by an oxygen atom. Exemplary of such groups are 2-oxaethylenephenyl (2-oxaphenethyl) and 3-oxapropylenephenyl.

A $C_1-C_6$ oxoalkyl group is a before discussed alkyl group in which $-CH_2-$ has been replaced by a carbonyl group. The presence of a $C_1-C_6$ oxoalkyl group provides an additional carbonyl; i.e., ketone or aldehyde, functionality to a compound of formula I. Exemplary $C_1$–$C_6$ oxoalkyl groups include 2-oxopropyl, 3-oxobutyl and 3-oxohexyl. Similarly, a $C_1$–$C_6$ halooxoalkyl group is a $C_1$–$C_6$ oxoalkyl group containing a further halogen substituent. An exemplary $C_1$–$C_6$ halooxoalkyl group is 1-chloro-2-oxopropyl.

A $C_1$–$C_3$ alkyl $C_1$–$C_3$ alkylenecarboxylate is a $C_1$–$C_3$ alkyl ester of a keto carboxylic acid of formula I in which the carboxyl group is separated from the illustrated carbonyl group of formula I by 1–3 carbons of the $C_1$–$C_3$ alkylene group. Exemplary groups include methyl carboxymethyl and methyl carboxyethyl.

It is also to be understood that the carbonyl group shown in formula I can be present in a ring containing five, six, or seven atoms that is free from unsaturation other than the depicted carbonyl. Put differently, R and $R^1$ of formula I together form a 5-, 6- or 7-membered ring that is free from unsaturation except for the depicted carboxyl group. The ring formed from R and $R^1$ can also include further substituents such as one or more alkyl groups, a halo group, a phenyl or an alkoxy carbonyl group as described above. In the case of phenyl and alkyl groups, those radicals can also be fused into the 5-7-membered ring so that a compound of formula I is present as a bicyclic ring system whose carbonyl group-containing ring has 5-7 atoms and whose fused ring contains an additional 1-4 carbon atoms. Exemplary compounds where R and $R^1$ together form such ring structures are shown hereinafter in Tables 1 and 2.

A carbonyl substrate of formula I has an overall length of three to about nine carbon atoms. That is to say that a carbonyl substrate is a compound having a length greater than that of acetone and less than that of about 5-nonanone. A more preferred length is about four to about six carbon atoms.

The radical chain lengths are measured along the longest linear carbon chain in the molecule. Where ring structures are present, that length is determined as a projection of the ring onto a plane. Thus, a cyclohexyl group has a "length" about equal to that of a butyl group. An atom in the chain other than carbon such as oxygen, sulfur or nitrogen is considered to have the size of carbon.

Such lengths can be readily determined by using published bond angles, bond lengths and atomic radii, as needed, to draw and measure a staggered chain, or by building models using commercially available kits whose bond angles, lengths and atomic radii are in accord with accepted, published values. Radical lengths can also be determined somewhat less exactly by assuming unsaturated bonds to have the same length as saturated bonds and that bond angles for unsaturated bonds are the same as those for saturated bonds, although the above-mentioned modes of measurement are preferred. The lengths are determined as the longest length for the compound.

As used herein, the phrase "R-configured alcohol" means that the hydroxyl group formed by reduction of the carbonyl group of the substrate has the R configuration.

Admixing comprises mixing each ingredient with each of the other ingredients in a suitable liquid medium to form a reaction mixture. Preferably, the liquid medium is an aqueous solvent. The reaction mixture is maintained under biological reaction conditions of temperature, pH, solvent osmolality, ionic composition and ambient atmosphere for a period of time sufficient to reduce the carbonyl substrate and form the R-configured alcohol.

Temperature can range from about 15° C. to about 40° C. Preferably temperature is from about 20° C. to about 40° C. and, more preferably from about 25° C. to about 37° C.

The pH value can range from about 6.0 to about 11.0. Preferably, the pH value is from about 6.5 to about 8.5 and, more preferably about 7.0 to about 7.5. The pH value is maintained by buffers in the liquid medium. The buffer is devoid of chelators that bind enzyme cofactors necessary for enzyme activity. The selection of a buffer is based on the ability of the buffer to maintain pH value at the desired level. Where the pH value is about 7.1, a preferred buffer is TRIS.

The osmolality and ionic composition of the aqueous solvent are designed and selected to solubilize the ingredients of the reaction mixture and to provide cofactors for the enzymes contained in the reaction mixture. The osmolality of the liquid medium preferably ranges from that of distilled water to that of one molar sodium chloride.

The reaction time and specific conditions for the formation of an R-configured alcohol vary with the nature of the carbonyl substrate.

The *Pseudomonas sp.* strain PED alcohol dehydrogenase used in the process of the present invention can accept a wide variety of ketone and aldehyde carbonyl substrates as discussed before in relation to formula I. Exemplary results for relative rates of reduction for a variety of ketone and aldehyde substrates are summarized below in Table 1.

TABLE 1

| Compound | | Relative rate[a] |
|---|---|---|
| 1 | 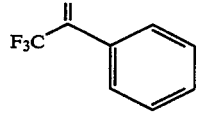 | 7 |
| 2 | 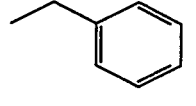 | 1[b] |
| 3 | 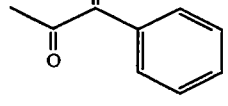 | 34 |
| 4 | 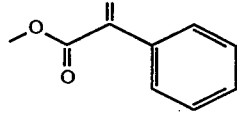 | 4 |
| 5 | 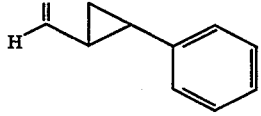 | 7 |
| 6 | 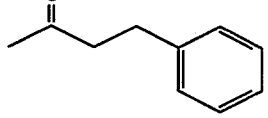 | 6 |

TABLE 1-continued

| Compound | Relative rate[a] |
|---|---|
| 7 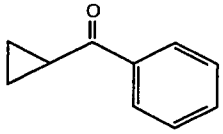 | <1 |
| 8 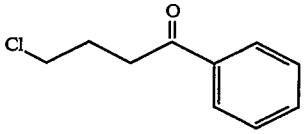 | 4 |
| 9 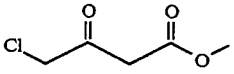 | 4 |
| 10 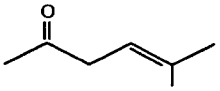 | 6 |
| 11 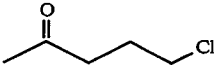 | 5 |
| 12 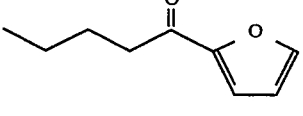 | <0.1 |
| 13 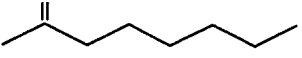 | 3 |
| 14 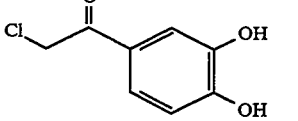 | <0.1 |
| 15 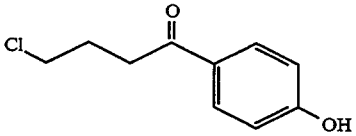 | 0 |
| 16 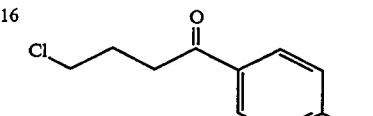 | 0 |
| 17 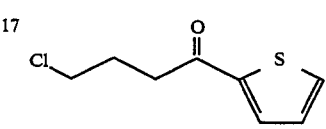 | 4 |
| 18 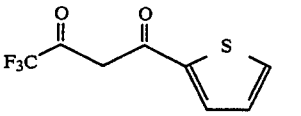 | 0 |
| 19 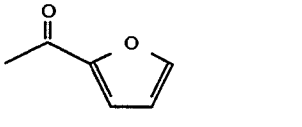 | 0 |
| 20 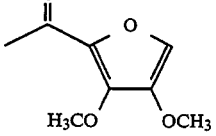 | 0.6 |
| 21 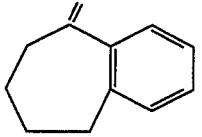 | 4 |

[a]Rates were determined by assaying with 10 mM ketone, 0.45 mM NADH, PED and monitoring the change in absorbance at 340 nm
[b]2.1 U/mg enzyme Previously described alcohol dehydrogenases, including the enzyme from *Pseudomonas sp.* strain SBD6, typically require that one of the chains of the carbonyl substrate is a methyl group. Although *Pseudomonas sp.* strain PED alcohol dehydrogenase can utilize such substrates, and R is preferably methyl, it is not necessary that the carbonyl substrate conform to such a structural limitation.

In addition to a methyl side chain, PED alcohol dehydrogenase of the present invention can utilize a variety of aromatic carbonyl compounds. Further, the position of the carbonyl group that is reduced by PED alcohol dehydrogenase need not be in a fixed position relative to that aromatic side chain. By way of example, 4-phenyl-2-butanone (Compound 6 from Table 1) is as good a substrate as is acetophenone (Compound 2 from Table 1).

PED alcohol dehydrogenase can accept a wide range of functional groups attached to the aliphatic ketones. By way of example, PED alcohol dehydrogenase can catalyze the reduction of terminal alkynyl ketones.

The *Pseudomonas sp.* strain PED alcohol dehydrogenase enzyme of the present invention can also reduce a wide variety of aliphatic and cyclic carbonyl substrates as shown in Table 2, below. This enzyme also does not reduce potential substrates that contain a carboxylic acid group, a ketone in a ring containing additional unsaturation, a substrate containing a silyl group, and substrates where the carbonyl group is exocyclic to a cyclic ring system.

TABLE 2

| Compound | Relative rate[a] |
|---|---|
| 22 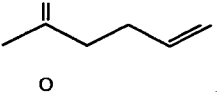 | 8 |
| 23 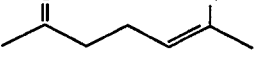 | 7 |
| 24  | 0 |
| 25 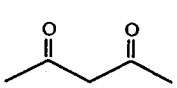 | 32 |

TABLE 2-continued

| Compound | | Relative rate[a] |
|---|---|---|
| 26 | 3-chloropentane-2,4-dione | 336 |
| 27 | methyl acetoacetate | 135 |
| 28 | hexane-2,5-dione | 9 |
| 29 | 4-oxopentanoic acid | 0 |
| 30 | 2-oxoheptanoic acid | 0 |
| 31 | methyl 2-oxocyclopentanecarboxylate | 22 |
| 32 | 2-methylcyclopentane-1,3-dione | 0 |
| 33 | ethyl 3-oxopentanoate | 6 |
| 34 | oct-1-en-3-one | 6 |
| 35 | octan-3-one | 2 |
| 36 | 1,3-dichloroacetone | 6 |
| 37 | 1-chlorobut-3-yn-2-one | 2 |
| 38 | methyl 6-oxohept-7-ynoate | <0.1 |
| 39 | hex-1-yn-3-one | 0 |
| 40 | 1-benzylpiperidin-4-one | 6 |
| 41 | (2-isopropyl-5-methyl)cyclohexanone | 3.4 |
| 42 | cyclohex-2-enone | 0 |
| 43 | 3-methylcyclohex-2-enone | 0 |
| 44 | R-C≡C-TMS ketone | 0 |
| 45 | 3-chlorobicyclic ketone | 2 |
| 46 | norbornenyl methyl ketone | 0 |
| 47 | norbornenone | 0 |
| 48 | phenoxyacetone | 7 |
| 49 | 3-(dimethylamino)-1-phenylpropan-1-one | 8 |
| 50 | 2,2-diethoxy-1-phenylethanone | <0.1 |

TABLE 2-continued

| Compound | | Relative rate[a] |
|---|---|---|
| 51 | phenyl propynone (PhC≡C-CO-CH₃) | <0.1 |
| 52 | 1-(2,3-dihydro-1,4-benzodioxin-6-yl)ethanone | 0 |
| 53 | 3-acetylindole | 0 |
| 54 | (E)-4-phenyl-3-buten-2-one | 0 |
| 55 | 2-acetyl-3,4-dihydronaphthalen-1(2H)-one | 0 |
| 56 | thiochroman-4-one | 0 |
| 57 | 2-acetylpyridine | 1.8 |
| 58 | propiophenone | <1 |
| 59 | 2-butanone | 100 |
| 60 | 2-pentanone | 6 |
| 61 | 2-hexanone | 5 |
| 62 | 2-heptanone | 5 |
| 63 | 3-hydroxy-2-butanone | 2 |
| 64 | 3-butyn-2-one | 1 |
| 65 | 3-chloro-2-butanone | 11 |
| 66 | cyclopropyl methyl ketone | 11 |
| 67 | 3-(methylthio)-2-butanone | 5 |
| 68 | 4-hydroxy-3-methyl-2-butanone | 0 |
| 69 | 1,1-dimethoxy-2-propanone | 5 |
| 70 | (E)-3-penten-2-one | <0.1 |
| 71 | (E)-4-methoxy-3-buten-2-one | 0 |

[a] relative rates were determined as described in Table 1

Exemplary products recovered from reductions carried out using PED alcohol dehydrogenase with a number of representative substrates are shown in Table 3, below. Analytical data for these reactions and the preparation of some of the substrates are provided hereinafter.

TABLE 3

| Substrate | Product[a] |
|---|---|
| PhCOCF₃  1 | Ph-CH(OH)-CF₃  1a |

TABLE 3-continued

| Substrate | Product[a] |
|---|---|
| 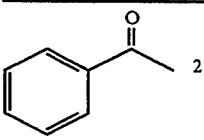 2 | 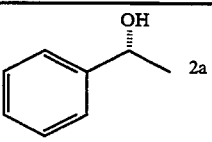 2a |
| 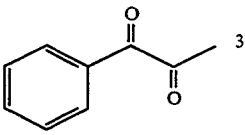 3 | 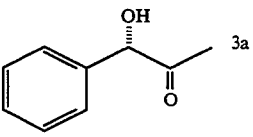 3a |
| 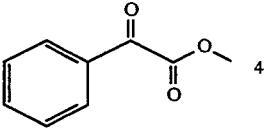 4 | 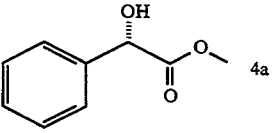 4a |
| 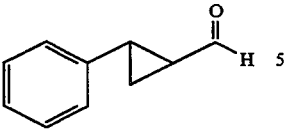 5 | 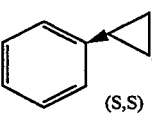 5a (S,S)    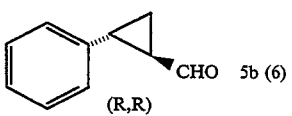 5b (6) (R,R) |
| 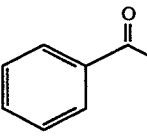 7 | 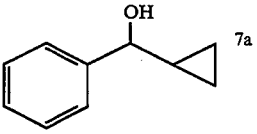 7a    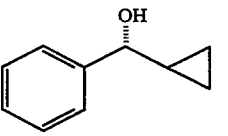 7b (8) |
| 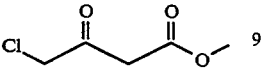 9 | 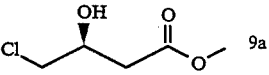 9a |
| 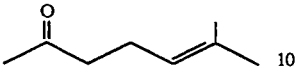 10 | 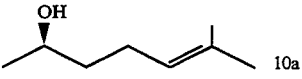 10a |
| 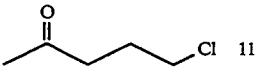 11 | 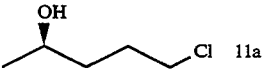 11a |
| 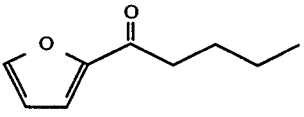 12 | 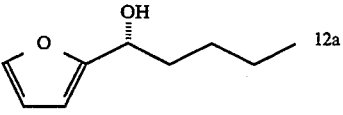 12a |
| 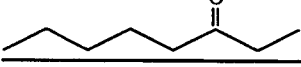 13 | 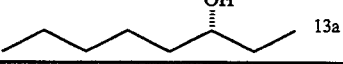 13a |

[a]Absolute configurations were determined by optical rotation

Aliphatic and aromatic (R) alcohols were formed in good enantiomeric excess. The carbonyl groups of 1-phenyl-1,2-propanedione (Compound 3) were reduced in a 6:1 ratio in favor of the carbonyl group proximal to the phenyl ring. Good enantioselectivity was seen when the carbonyl was flanked by a methyl group (Compound 2) or bulkier groups (Compounds 4 and 9). PED alcohol dehydrogenase-catalyzed reduction of the transphenylcyclopropyl carboxaldehyde (Compound 5) discriminated fairly well between the two enantiomers. In all cases, the reductions proceeded in high enantiomeric excess except for 3-octanone (Compound 13), where the enzyme did not distinguish between the ethyl and pentyl side chains efficiently.

This enzyme has excellent stability under reaction conditions, obviating the need for immobilization. However, the long term (e.g. 60–80 hours) stability of PED alcohol dehydrogenase can be enhanced by including low concentrations of an organic solvent, e.g. about 5 to about 10 volume percent 2-propanol, in the aqueous reaction mixture.

In a preferred embodiment, the NADH used in the process of the present invention can be regenerated in the same reaction mixture used to make the R-configured alcohol. The NADH is regenerated from a cofactor alcohol substrate via a PED alcohol dehydrogenase catalyzed transfer of a hydride ion from that cofactor alcohol substrate to NAD to form NADH. Preferably, that cofactor alcohol substrate is ethanol, 1-propanol or 2-propanol. 2-Propanol is most preferred.

Alternatively, that cofactor alcohol substrate can be an R-configured alcohol according to formula Ia, hereinafter. Such a cofactor alcohol substrate is, however, not preferred. Where the cofactor alcohol substrate is an R-configured alcohol according to formula Ia, the alcohol used as the cofactor is different from the R-configured alcohol formed in the process of the present invention. The cofactor alcohol substrate is selected so as to not interfere with either the production or the recovery of the R-configured alcohol formed.

Thus, in another aspect, the present invention provides a process of forming an R-configured alcohol with the regeneration of NADH, which process comprises the steps of (a) forming a reaction mixture by admixing in a liquid medium (i) a catalytic amount of NAD, (ii) a catalytic amount of a PED alcohol dehydrogenase preparation, (iii) a cofactor alcohol substrate and (iv) a carbonyl substrate of the formula I, above; and (b) maintaining said reaction mixture under biological reaction conditions and for a time period sufficient to reduce said carbonyl substrate and form said R-configured alcohol.

In accordance with this embodiment, PED alcohol dehydrogenase constitutes a good example of a one enzyme catalyzed reaction, where a single enzyme (i.e., PED alcohol dehydrogenase) is responsible for a desired reaction as well as cofactor regeneration. Similarly, PED alcohol dehydrogenase can also serve to regenerate NAD in a process for transferring a hydride ion from an R-configured alcohol to the pro-R face of NAD, which process is set forth hereinafter. In accordance with such a process, NAD is regenerated from a cofactor aldehyde or ketone substrate and PED alcohol dehydrogenase. Preferably, the cofactor aldehyde or ketone substrate is acetone.

In all embodiments of the process of the present invention, the formed R-configured alcohol is preferably recovered. Methods of recovering alcohols from liquid media are well known in the art. Exemplary of such methods are high pressure liquid chromatography and column chromatography over silica gel using an appropriate organic solvent as the mobile phase.

2. A process of Transferring a Hydride ion to the pro-R Face of NAD

In a manner analogous to that of other alcohol dehydrogenases, PED alcohol dehydrogenase can catalyze the oxidation of alcohols as well as the reduction of carbonyl substrates. Thus, PED alcohol dehydrogenase can be used in a process to oxidize R-configured alcohols. Because PED alcohol dehydrogenase has specificity for the pro-R face of NAD, the oxidation of an alcohol involves the transfer of a hydride ion to the pro-R face of NAD.

In accordance with such a method, a reaction mixture is formed by admixing in a liquid medium (i) NADH, (ii) a catalytic amount of a PED alcohol dehydrogenase preparation and (iii) an R-configured alcohol of the formula Ia, below:

$$R\text{---}R^2COH\text{---}R^1 \qquad \text{Ia}$$

wherein R and $R^1$ and the length of the R-configured alcohol are as defined above and $R^2$ is hydrogen, deuterium or tritium.

As noted above, R, $R^1$ and the total chain length of an alcohol substrate of formula Ia are the same as those discussed hereinbefore in relation to a carbonyl substrate of formula I. It will be apparent to the skilled worker, however, that inasmuch as a substrate of formula Ia is an alcohol, the prior comments as to the structural type of ketone substrate must be interpreted as relating to an alcohol for a substrate of formula Ia. For example, where $R^1$ of formula I was a $C_1$-$C_6$ acyl group, that substrate was described as an α-diketone, whereas the same $R^1C_1$-$C_6$ acyl group present in a substrate of formula Ia provides an α-hydroxy ketone.

The reaction mixture is then maintained under biological reaction conditions and for a time period sufficient to oxidize the R-configured alcohol, as discussed previously.

The transfer of a hydride ion to NAD and oxidation of the R-configured alcohol results in the formation of a ketone or aldehyde carbonyl compound as well as the formation of NADH.

In a preferred embodiment, the hydride ion is deuteride ($D^-$) or tritide ($T^-$). Where the hydride ion is ($D^-$) or ($T^-$), the R-configured alcohol substrate used in the method contains deuterium or tritium, respectively, as the hydrogen component of the alcohol hydroxyl group that is oxidized. Deuterium or tritium labelled alcohols can be obtained from commercial sources or made using standard methods well known in the art.

Because the PED alcohol dehydrogenase used in the process of the present invention adds hydride ion to the pro-R face of NAD, where that hydride ion is ($D^-$) or ($T^-$), the formed NADH has deuterium or tritium, respectively, only at the pro-R face of the nicotinamide ring. In this regard, the process of the present invention can be used to specifically label the pro-R face of NADH with deuterium or tritium. That labeled NADH can then be used to study the mechanism of alcohol dehydrogenase activity using any enzyme and carbonyl substrate.

The stereochemical mechanism of PED alcohol dehydrogenase with respect to NAD was determined by the enzyme catalyzed transfer of a deuteride ion from 2-propanol-$d_8$ to NAD followed by NMR analysis (See Example 3, hereinafter). Because the diastereotopic hydrogens at C4 of NADH differ by 0.1 ppm (2.77 ppm for the pro-R facial hydrogen and 2.67 ppm for the pro-S facial hydrogen) the transfer of a deuteride ion to NAD will show a single peak representative of the stereochemistry of hydride transfer. Arnold et al., *Biochemistry*, 15: 4844 (1976).

PED alcohol dehydrogenase transfers the deuteride (and analogously the hydride) to and from the re face of the cofactor as determined by the finding of a single NMR peak at 2.67 ppm.

In a preferred embodiment, the NADH formed by a process of the present invention is recovered. Methods of recovering NADH from liquid media are well known in the art. Exemplary of such methods is column chromatography using DEAE-Sepharose.

The following examples illustrate particular embodiments of the invention and are not limiting of the specification and claims in any way.

EXAMPLES

Example 1

Isolation and Purification of *Pseudomonas sp.* strain PED

The microorganism was enriched in a screening medium containing (per liter): 1.0 g $NH_4Cl$, 0.5 g $CaCl_2\cdot H_2O$, 0.5 g $MgSO_4H_2O$, 1.0 g NaCl, 2.1 g $NaH_2$-

PO$_4$H$_2$O, 0.3 g K$_2$HPO$_4$, 0.2 g yeast extract, and 10 milliliters (ml) trace mineral solution. The trace mineral solution contained (per liter): 12.8 g nitriloacetic acid, 0.1 g FeSO$_4$H$_2$O, 0.1 g MnCl$_2$4H$_2$O, 0.2 g CoCl$_2$H$_2$O, 0.1 g CaCl$_2$H$_2$O, ZnCl$_2$2H$_2$O, 0.02 g CuCl$_2$2H$_2$O, 0.01 g H$_3$BO$_3$, 0.01 g Na$_2$MoO$_4$2H$_2$O, 1.0 g NaCl, 0.02 g Na$_2$SeO$_3$, 0.03 g NiSO$_4$6H$_2$O, and Na$_2$WO$_4$. The pH of the medium was adjusted to 7.0. ($\pm$)-1-Phenyl-1,2-ethanediol was added as carbon and energy source (0.5 percent w/v).

The enrichment was carried out at 30° C. with shaking (250 rpm) in 125 ml serum bottles containing 70 ml of the screening medium and 0.1 g of garden soil as the source of microorganisms. The enrichments that showed growth were then plated onto agar plates prepared from the screening medium containing 1.5 percent agar. Subsequently, single colonies were transferred into serum bottles containing 20 ml of the same medium. These procedures were repeated several times and finally the cultures were plated on LB agar plates (10 g tryptone, 5 g yeast extract, 0.5 g NaCl, and 15 g agar per liter distilled water, pH 7.0) to ensure homogeneity of the colonies.

One bacterial strain exhibiting prodigious growth was chosen for further study. The microorganisms of that substantially pure strain are obligate aerobe short rods, 1–1.5 $\mu$M in diameter. The gram negative colonies are cream color with a smooth edge and surface. Physiological characterization was carried out with an oxyferm tube kit and according to established procedures. The following are not characteristics of strain PED: OF anaerobic dextrose, H$_2$S formation, indole formation, and urease. The following characteristics are positive for strain PED: arginine dihydrolase, OF xylose, OF aerobic dextrose, citrate utilization and oxidase activity. Thus, the microorganism belongs to *Pseudomonas sp.* and is arbitrarily designated as strain PED. All purification steps were carried out at 4° C. unless stated otherwise.

Example 2

Isolation and Purification of PED Alcohol Dehydrogenase

A single colony of *Pseudomonas sp.* strain PED, prepared according to the procedures of Example 1, was transferred to a serum bottle containing 20 ml of the screening medium. The growing culture was then transferred to a 3 L flask containing 1 L of the same medium with 0.5 percent 1-phenyl-1,2-ethanediol. The culture was cultivated at 30° C. with shaking (250 rpm) and monitored by measuring optical density at 660 nm.

Cell cultures obtained during the late exponential growth phase were harvested by centrifugation at 8000 rpm for 20 minutes. The wet cells (17.5 g) were suspended in 87 ml 30 mM TRIS buffer, pH 7, containing 4 mM dithiothreitol (DTT) and ruptured in a SLM Aminco French Press (23,000 psi).

A cell extract was obtained as the supernatant after centrifugation at 15000 rpm for 75 minutes. The 20–60 percent ammonium sulfate pellet obtained by adding solid ammonium sulfate was dialyzed for five hours versus 30 mM TRIS buffer, pH 7.5 containing 4 mM DTT (buffer A) and applied to a previously equilibrated DEAE-Sepharose CL6B column (2.5$\times$60 cm) in buffer A. After the nonbinding components were eluted as determined by absorbance at 254 nm, a 0–200 mM ammonium sulfate gradient in buffer A was begun (total volume 1 L).

The tubes containing NAD dependent ($\pm$)-1-phenyl-1,2-ethanediol and 2-propanol oxidizing activity were collected, concentrated in an Amicon protein concentrator, and applied to an Ultragel AcA34 gel filtration column (5$\times$125 cm) in buffer A. The fractions containing activity were combined, concentrated, and applied to a 5 cm$^3$ $\beta$-NAD agarose affinity column (attached through N6 with an 8 carbon spacer). After washing the column with buffer A, the enzyme was eluted with 10 mM NAD in buffer A.

From 17 g of wet cells (5.1 g protein) containing 710 U based on 2-propanol, 5 mg of enzyme with a total activity of 180 U was isolated.

Example 3

Stereochemical Mechanism of PED Alcohol Dehydrogenase

A reaction mixture was formed by admixing 1 ml 2-propanol-d$_8$ and 150 mg NAD in 45 ml of a 100 mM ammonium bicarbonate buffer, pH 8. Purified PED alcohol dehydrogenase (20 units) was enclosed in a dialysis bag and placed in the reaction mixture. After two days, the reaction was 80 percent complete. The dialysis bag was removed and rinsed with distilled water. The combined aqueous layers were lyophilized to form a white powder.

The white powder was applied to a DEAE cellulose column (2$\times$16 cm) previously equilibrated with 25 mM ammonium bicarbonate, pH 8. NAD was eluted with 50 mM ammonium bicarbonate and the reduced cofactor was eluted with 250 mM ammonium bicarbonate buffer, both pH 8. The NADH fractions were combined and lyophilized. $^1$H NMR (D$_2$O) 2.67 ppm (s, 1H).

The finding of a single NMR peak at 2.67 ppm indicates that PED alcohol catalyses the transfer of a hydride ion from an alcohol substrate to the pro-R face of NAD.

Example 4

Synthesis of R-configured Alcohols

A. General Materials and Methods

All chemicals were purchased from commercial sources (e.g. Aldrich, Fisher, or Sigma). Nuclear magnetic resonance (NMR) spectra were recorded on a 300 MHz spectrometer. ($-$)-$\alpha$-Methoxy-$\alpha$-trifluoromethylphenylacetyl chloride was obtained from Fluka. For the determination of enantiomeric excess, the alcohols were converted to ($-$)-$\alpha$-methoxy-$\alpha$-trifluoromethylphenylacetic acid esters (MTPA esters) and analyzed by NMR spectroscopy, by HPLC analysis on a Daicel chiralcel OB column, or by comparison of the optical rotations versus known compounds. Dale et al., *J. Org. Chem.*, 34: 2543 (1969). The optical rotations were determined with 10 cm path length cells.

B. Enzyme Assays

*Pseudomonas sp.* strain PED alcohol dehydrogenase enzyme assays were done by combining appropriate aliquots of the following solutions and monitoring at 340 nm ($\epsilon_{NADH}$ 6.22 L mol$^{-1}$ cm$^{-1}$): 50 mM TRIS buffer pH 7.1, 0.45 mM NADH and 10 mM of an appropriate carbonyl substrate. Five percent by weight (v/v) of dimethylformamide (DMF) was added to aid substrate solubility.

The enzyme was prepared by suspending the wet cells in 50 mM phosphate buffer, pH 7.5 (1 g wet cells/5 ml buffer), breaking in an Amicon SLM French press (23,000 psi) and centrifuging at 15000 rpm for 75 minutes. The supernatant was lyophilized and used as the source of enzyme.

C. Synthesis of (S)-1-Phenyl-2,2,2-trifluoroethanol (Compound 1a)

A reaction mixture was formed by admixing (i) 50 mg NAD, (ii) 4 ml of 2-propanol and (iii) 5 mmoles of trifluoroacetophenone, Compound 1, in a liquid medium containing 1 gm of lyophilized PED alcohol dehydrogenase preparation, 75 ml of 50 mM phosphate buffer, pH 7.1, and 25 ml of hexane. The pH of the reaction was maintained constant by addition of 1N NaOH.

The reaction mixture was maintained at room temperature until product formation stopped. When product formation stopped, (S)-1-phenyl-2,2,2-trifluoroethanol, Compound 1a, was isolated by removal of the hexane layer and extraction of the aqueous layer with ethyl ether (3×75 ml).

The combined organic layers were dried over sodium sulfate, evaporated and the residue purified on silica gel (hexane/ethyl ether) to yield the title compound in 37 percent yield.

A 92 percent enantiomeric excess (ee) was determined by HPLC on a chiralcel OB column 98:2 hexane:2-propanol. With a flow rate of 1 ml/minute the retention times were 10.42 minutes for (−)(R) and 11.26 minutes for (+)(S). $^1$H NMR (CDCl$_3$) δ 3.15 (s, 1H); 4.95 (q, 1H); 7.40 (m, 5H). The spectroscopic properties were the same as determined previously. Peters et al., *J. Org. Chem*, 33: 4245 (1968).

D. Synthesis of (R)-1-Phenylethanol (Compound 2a)

A reaction mixture was formed by admixing (i) 50 mg NAD, (ii) 4 ml of 2-propanol and (iii) 5 mmoles of acetophenone, Compound 2, in a liquid medium containing 1 gm of lyophilized PED alcohol dehydrogenase preparation, 75 ml of 50 mM phosphate buffer, pH 7.1, and 25 ml of hexane. The pH of the reaction was maintained constant by addition of 1N NaOH. The reaction mixture was maintained at room temperature until product formation stopped. When product formation stopped, (R)-1-Phenylethanol, Compound 2a, was isolated by removal of the hexane layer and extraction of the aqueous layer with ethyl ether (3×75 ml).

The combined organic layers were dried over sodium sulfate, evaporated and the residue purified on silica gel (hexane/ethyl ether) to yield the title compound in 34 percent yield.

More than a 97 percent ee was determined by conversion to a MTPA ester and comparison of the methoxy and methyl group integrations. $[α]_D^{20}$ +50.3 (c=6.7, CDCl$_3$) $^1$H NMR CDCl$_3$ δ 1.47 (d, 3H); 2.25 (s, 1H); 4.79 (quartet, 1H); 7.28 (m, 5H). $^1$H NMR was identical to the commercially available racemic compound. Absolute configuration was determined by literature assignments of optical rotation. Ziffer et al., *J. Org. Chem.*, 48:3017 (1873).

E. Synthesis of (R)-1-Hydroxy-1-phenyl-2-propanone (Compound 3a)

A reaction mixture was formed by admixing (i) 50 mg NAD, (ii) 4 ml of 2-propanol and (iii) 5 mmoles of 1-phenyl-1,2-propanedione, Compound 3, in a liquid medium containing 1 gm of lyophilized PED alcohol dehydrogenase preparation, 75 ml of 50 mM phosphate buffer, pH 7.1, and 25 ml of hexane. The pH value of the reaction was maintained constant by addition of 1N NaOH. The reaction mixture was maintained at room temperature until product formation stopped. When product formation stopped, (R)-1-hydroxy-1-phenyl-2-propanone, Compound 3a, was isolated by removal of the hexane layer and extraction of the aqueous layer with ethyl ether (3×75 ml).

The combined organic layers were dried over sodium sulfate, evaporated and the residue purified on silica gel (hexane/ethyl ether) to yield the title compound in 83 percent yield.

86 Percent ee was determined by conversion to a MTPA ester and comparison of the methoxy peaks. $^1$H NMR (CDCl$_3$) δ 2.08 (s, 3H); 5.11 (s, 1H); 7.37 (m, 5H). $^1$H NMR was the same as reported previously and showed a 6:1 ratio for the two regioisomers (1-hydroxy-1-phenyl-2-propanone: 2-hydroxy-1-phenyl-1-propanone). Davis et al., *Tetrahedron Lett.*, 30: 779 (1989). Absolute configuration was determined by comparison of literature assignments of optical rotation for the (S) enantiomer. Fuganti et al. *J. Chem. Soc. Chem. Commun.*, 1619 (1988).

F. Synthesis of (R)-Methyl mandelate (Compound 4a)

A reaction mixture was formed by admixing (i) 50 mg NAD, (ii) 4 ml of 2-propanol and (iii) 5 mmoles of methyl benzoylformate, Compound 4, in a liquid medium containing 1 gm of lyophilized PED alcohol dehydrogenase preparation, 75 ml of 50 mM phosphate buffer, pH 7.1, and 25 ml of hexane. The pH of the reaction was maintained constant by addition of 1N NaOH. The reaction mixture was maintained at room temperature until product formation stopped. When product formation stopped, (R)-methyl mandelate, Compound 4a, was isolated by removal of the hexane layer and extraction of the aqueous layer with ethyl ether (3×75 ml).

The combined organic layers were dried over sodium sulfate, evaporated and the residue purified on silica gel (hexane/ethyl ether) to yield the title compound in 79 percent yield.

More than a 97 percent ee was determined conversion to the MTPA ester and comparison of the methoxy peaks. $[α]_D^{25}$ +173 (c=2.18, CHCl$_3$). $^1$H NMR (CDCl$_3$) δ 3.76 (s, 3H); 5.20 (d, 1H); 7.44 (m, 5H). $^1$H NMR was the same as the commercially available sample. Absolute stereochemistry was assigned based on the literature values of optical rotation. Ziffer et al., *J. Org. Chem.*, 48:3017 (1983).

G. Synthesis of (S,S)-2-Phenylcyclo-propylmethanol (Compound 5a)

A reaction mixture was formed by admixing (i) 50 mg NAD, (ii) 4 ml of 2-propanol and (iii) 5 mmoles of 1-carboxyaldehyde-2-phenylcyclopropane (Example 5), Compound 5, in a liquid medium containing 1 gm of lyophilized PED alcohol dehydrogenase preparation, 75 ml of 50 mM phosphate buffer, pH 7.1, and 25 ml of hexane. The pH of the reaction was maintained constant by addition of 1N NaOH. The reaction mixture was maintained at room temperature until product formation stopped. When product formation stopped, (S,S)-2-phenylcyclo-propylmethanol, Compound 5a, was isolated by removal of the hexane layer and extraction of the aqueous layer with ethyl ether (3×75 ml).

The combined organic layers were dried over sodium sulfate, evaporated and the residue purified on silica gel (hexane/ethyl ether) to yield the title compound in 36 percent yield.

65 Percent enantiomeric excess was determined by HPLC on chiralcel OB column 95:5 hexane:2-propanol, with a flow rate of 1 ml/minute the retention times were 9.68 minutes for (−)(R,R) and 10.88 minutes for (+)(S,S). $^1$H NMR (CDCl$_3$) δ 0.7–2.0 (m, 4H); 2.8 (s, 1H); 3.5 (d, 2H); 7.1 (m, 5H). $^1$H NMR was identical to the previously reported data. Absolute stereochemistry of the all trans products were determined by comparison of optical rotation versus known compounds. See, e.g., Yasui et al. *J. Am. Chem. Soc.*, 109:2311 (1987); and Mori et al., *Tetrahedron*, 42: 6447 (1986).

H. Synthesis of Phenylcyclopropyl methanol (Compound 7a)

A reaction mixture was formed by admixing (i) 50 mg NAD, (ii) 4 ml of 2-propanol and (iii) 5 mmoles of phenyl cyclopropyl ketone, Compound 7, in a liquid medium containing 1 gm of lyophilized PED alcohol dehydrogenase preparation, 75 ml of 50 mM phosphate buffer, pH 7.1, and 25 ml of hexane. The pH value of the reaction was maintained constant by addition of 1N NaOH. The reaction mixture was maintained at room temperature until product formation stopped. When product formation stopped, phenylcyclopropyl methanol, Compound 7a, was isolated by removal of the hexane layer and extraction of the aqueous layer with ethyl ether (3×75 ml).

The combined organic layers were dried over sodium sulfate, evaporated and the residue purified on silica gel (hexane/ethyl ether) to yield the title compound in 41 percent yield.

92 Percent ee was determined by conversion to a MTPA ester and comparison of the methoxy peaks. $[\alpha]_D^{25}$ +27.99° (c=1.072, CHCl$_3$). $^1$H NMR (CDCl$_3$) δ 7.25–7.44 (m, 5H); 3.98–4.00 (d, 1H); 1.19–1.29 (m, 1H); 0.37–0.65 (m, 4H). $^1$H NMR is consistent with commercially available compound.

I. Synthesis of (S)-Methyl-4-chloro-3-hydroxybutanoate (Compound 9a)

A reaction mixture was formed by admixing (i) 50 mg NAD, (ii) 4 ml of 2-propanol and (iii) 5 mmoles of methyl 4-chloro-3-oxobutanoate, Compound 9, in a liquid medium containing 1 gm of lyophilized PED alcohol dehydrogenase preparation, 75 ml of 50 mM phosphate buffer, pH 7.1, and 25 ml of hexane. The pH of the reaction was maintained constant by addition of 1N NaOH. The reaction mixture was maintained at room temperature until product formation stopped. When product formation stopped, (S)-methyl 4-chloro-3-hydroxybutanoate, Compound 9a, was isolated by removal of the hexane layer and extraction of the aqueous layer with ethyl ether (3×75 ml).

The combined organic layers were dried over sodium sulfate, evaporated and the residue purified on silica gel (hexane/ethyl ether) to yield the title compound in 76 percent yield.

More than a 98 percent ee was determined by conversion to a MTPA ester and comparison of the methoxy peaks. $[\alpha]_D^{25}$ 21.64° (c=0.67 CHCl$_3$). $^1$H NMR (CDCl$_3$) δ 2.65 (dd, 2H); 3.62 (dd, 2H); 3.74 (s, 3H); 4.28 (m, 1H). Absolute configuration was determined by comparison versus published values for optical rotation. Zhou et al., *J. Am. Chem. Soc.*, 105: 5925 (1983).

J. Synthesis of (R)-6-Methyl-5-hepten-2-ol (Compound 10a)

A reaction mixture was formed by admixing (i) 50 mg NAD, (ii) 4 ml of 2-propanol and (iii) 5 mmoles of 6-methyl-5-hepten-2-one, Compound 10, in a liquid medium containing 1 gm of lyophilized PED alcohol dehydrogenase preparation, 75 ml of 50 mM phosphate buffer, pH 7.1, and 25 ml of hexane. The pH value of the reaction was maintained constant by addition of 1N NaOH. The reaction mixture was maintained at room temperature until product formation stopped. When product formation stopped, (R)-6-methyl-5-hepten-2-ol, Compound 10a, was isolated by removal of the hexane layer and extraction of the aqueous layer with ethyl ether (3×75 ml).

The combined organic layers were dried over sodium sulfate, evaporated and the residue purified on silica gel (hexane/ethyl ether) to yield the title compound in 51 percent yield.

More than a 97 percent ee was determined by conversion to a MTPA ester and comparison of the methoxy and methyl peaks. $[\alpha]_D^{23}$ −14.9° (c=1.66 CDCl$_3$). $^1$H NMR (CDCl$_3$) δ 1.22 (d, 3H); 1.52 (m, 2H); 1.65 (s, 3H); 1.71 (s, 3H); 2.08 (m, 2H); 3.83 (m, 1H); 5.15 (t, 1H). $^1$H NMR is consistent with the commercially available compound. Absolute configuration was assigned by comparison of the optical rotation for the (S) enantiomer. Keinan et al., *J. Am. Chem. Soc.*, 108: 162 (1986).

K. Synthesis of (R)-5-Chloro-2-pentanol (Compound 11a)

A reaction mixture was formed by admixing (i) 50 mg NAD, (ii) 4 ml of 2-propanol and (iii) 5 mmoles of 5-chloro-2-pentanone, Compound 11, in a liquid medium containing 1 gm of lyophilized PED alcohol dehydrogenase preparation, 75 ml of 50 mM phosphate buffer, pH 7.1, and 25 ml of hexane. The pH of the reaction was maintained constant by addition of 1N NaOH. The reaction mixture was maintained at room temperature until product formation stopped. When product formation stopped, (R)-5-chloro-2-pentanol, Compound 11a, was isolated by removal of the hexane layer and extraction of the aqueous layer with ethyl ether (3×75 ml).

The combined organic layers were dried over sodium sulfate, evaporated and the residue purified on silica gel (hexane/ethyl ether) to yield the title compound in 48 percent yield.

93 Percent ee was determined by conversion to a MTPA ester and comparison of the methoxy and methyl peaks. $[\alpha]_D^{23}$ −14.9° (c=0.19, CDCl$_3$). $^1$H NMR (CDCl$_3$) δ 1.23 (d, 3H); 1.62 (m, 2H); 1.88 (m, 2H); 3.59 (t, 2H); 3.86 (m, 1H). Absolute configuration was assigned based on literature values of optical rotation of the (S) enantiomer. Keinan et al., *J. Am. Chem. Soc.*, 108: 3474 (1986).

L. Synthesis of (R)-α-Butyl-2-furanmethanol (Compound 12a)

A reaction mixture was formed by admixing (i) 50 mg NAD, (ii) 4 ml of 2-propanol and (iii) 5 mmoles of butyl 2-furanoyl ketone, Compound 12, in a liquid medium containing 1 gm of lyophilized PED alcohol dehydrogenase preparation, 75 ml of 50 mM phosphate buffer, pH 7.1, and 25 ml of hexane. The pH of the reaction was maintained constant by addition of 1N NaOH. The reaction mixture was maintained at room temperature until product formation stopped. When product formation stopped, (R)-α-butyl-2-furanmethanol, Compound 12a, was isolated by removal of the hexane layer and extraction of the aqueous layer with ethyl ether (3×75 ml).

The combined organic layers were dried over sodium sulfate, evaporated and the residue purified on silica gel (hexane/ethyl ether) to yield the title compound in 5-10 percent yield.

45 Percent ee was determined by conversion to a MTPA ester. $^1$H NMR (CDCl$_3$) δ 0.91 (m, 3H); 1.34 (m, 4H); 1.86 (m, 2H); 4.68 (t, 1H); 6.24 (d, 1H); 6.31 (m, 1H); 7.36 (d, 1H). $^1$H NMR is consistent with previously reported data. Amouroux et al., *J. Heterocycl. Chem.*, 18:565 (1981) . Absolute stereochemistry was assigned in accord with published values of optical rotation. Kametani et al., J. Chem. Soc. Perkin Trans. I 1990, 639.

M. Synthesis of (R)-3-Octanol (Compound 13a)

A reaction mixture was formed by admixing (i) 50 mg NAD, (ii) 4 ml of 2-propanol and (iii) 5 mmoles of (R)-3-octanone, Compound 13, in a liquid medium containing 1 gm of lyophilized PED alcohol dehydrogenase preparation, 75 ml of 50 mM phosphate buffer, pH 7.1, and 25 ml of hexane. The pH value of the reaction was maintained constant by addition of 1N NaOH. The reaction mixture was maintained at room temperature until product formation stopped. When product formation stopped, (R)-3-octanol, Compound 13a, was isolated by removal of the hexane layer and extraction of the aqueous layer with ethyl ether (3×75 ml).

The combined organic layers were dried over sodium sulfate, evaporated and the residue purified on silica gel (hexane/ethyl ether) to yield the title compound in 43 percent yield.

27 Percent ee was determined by comparison of optical rotation. $[α]_D^{20}$ −3.5° (c=1.1 CHCl$_3$) $^1$H NMR (CDCl$_3$) δ 0.86 (m, 6H); 1.22 and 1.38 (m, 10 H); 3.48 (m, 1H). $^1$H NMR is consistent with commercially available compound. Absolute configuration was determined by comparison of literature values of optical rotation. Kirchner et al., *J. Am. Chem. Soc.*, 107: 7072 (1985).

Example 5

PED Catalyzed Oxidation of Alcohols

A. Enzyme Assays

*Pseudomonas sp.* strain PED alcohol dehydrogenase enzyme assays were done by combining appropriate aliquots of the following solutions and monitoring at 340 nm ($ε_{NADH}$ 6.22 L mol$^{-1}$ cm$^{-1}$): 50 mM TRIS buffer pH 8.5, 5 mM NAD and 10 mM of an appropriate alcohol. Five percent by weight (v/v) of dimethylformamide (DMF) was added to aid substrate solubility.

The enzyme was prepared by suspending the wet cells in 50 mM phosphate buffer, pH 7.5 (1 g wet cells/5 ml buffer), breaking in an Amicon SLM French press (23,000 psi) and centrifuging at 15000 rpm for 75 minutes. The supernatant was lyophilized and used as the source of enzyme.

B. Synthesis of 1-carboxaldehyde-2-phenylcyclopropane (Compound 5)

About 152 g (272 mmole) of potassium hydroxide was dissolved in 400 ml water at zero degrees C. The reaction was layered with 400 ml ethyl ether and 20 g (136 mmole) 1-methyl-3-nitro-1-nitroso-guanidine were added and stirred until evolution of gas ceased (25 minutes). The ether layer was removed and the aqueous layer washed with 1×150 ml ether. The fresh yellow CH$_2$N$_2$ solution was added in small portions to 20 g 1-carboxylate-2-phenylcyclopropane in 200 ml dry ether until the yellow color stayed for a few minutes.

The solvent was evaporated and the methyl ester purified by silica gel chromatography 1:2 hexane:ethyl ether. Yield 18.5 g (105 mmole), 85 percent.

About 4.0 g (23 mmole) of the methyl ester in 100 ml anhydrous ether were cooled in a liquid nitrogen/methanol/ethyl ether bath in a three neck flask. Fifty-seven (57) ml (57 mmole) of 1M diisobutylaluminum hydride in hexane were added dropwise over four hours, not allowing the temperature inside the flask to reach above −100° C. Water (7 ml) was added to quench the reaction immediately followed by Rochelies salt, and the resulting mixture was permitted to warm to room temperature. The reaction was extracted 3×125 ml ethyl ether. The dried ether extracts were evaporated and chromatographed on silica gel (1:1 hexane:ethyl ether) to yield 2.69 g (80 percent).

$^1$H NMR (CDCl$_3$) δ 1.48 (m, 1H); 1.66 (m, 1H); 2.12 (m, 1H); 2.58 (m, 1H); 7.20 (m, 5H); 9.24 (m, 1H). $^1$H NMR are consistent with literature values. Mori et al., *Tetrahedron*, 42: 6447 (1986).

Example 6

Synthesis of Terminal Alkynyl Ketone Carbonyl Substrates of Table 2

A. Synthesis of 1-Butyn-3-one (Compound 64)

The following were combined in a dry flask under nitrogen at zero degrees C; 23 mmole bis(trimethylsilyl)acetylene, 23 mmole of an acid chloride and 80 ml dichloromethane. 3.07 g aluminum trichloride was added over 35 minutes under nitrogen at zero degrees C. The reaction was stirred overnight and allowed to warm to room temperature. The excess aluminum trichloride was destroyed by addition of 100 ml 1N HCl followed by extraction with 3×100 ml ethyl ether.

The dried organic layers (Na$_2$SO$_4$) were evaporated and the residue was purified by vacuum distillation or silica gel chromatography (1:9 ethyl ether:hexane). The trimethyl silyl group was removed by adding 15 ml 0.1M borax to a solution of 1-butyn-3-one (1 g) in 80 ml methanol. The solution was permitted to sit at room temperature for 15 minutes and was quenched with 75 ml ice cold 1N HCl. Ethyl ether extractions 3×75 ml of the aqueous composition were dried (Na$_2$SO$_4$) and evaporated to dryness. Purification was accomplished by either vacuum distillation or silica gel chromatography (1:4 ethyl ether:hexane).

66 Percent yield. $^1$H NMR (CDCl$_3$) δ 2.39 (s, 3H); 3.27 (s, 1H). $^1$H NMR consistent with commercial sample.

B. Synthesis of 1-Hexyn-3-one (Compound 39)

The following were combined in a dry flask under nitrogen at zero degrees C; 23 mmole bis(trimethylsilyl)acetylene, 23 mmole of an acid chloride and 80 ml dichloromethane. 3.07 g aluminum trichloride were added over 35 minutes under nitrogen at zero degrees C. The reaction was stirred overnight (about 18 hours) and permitted to warm to room temperature. The excess aluminum trichloride was destroyed by addition of 100 ml 1N HCl followed by extraction with 3×100 ml ethyl ether.

The dried organic layers (Na$_2$SO$_4$) were evaporated and the residue was purified by vacuum distillation or silica gel chromatography (1:9 ethyl ether:hexane). The trimethyl silyl group was removed by adding 15 ml 0.1M borax to a solution of 1-hexyn-3-one (1 g) in 80 ml methanol. The solution was kept at room temperature for 15 minutes and quenched with 75 ml ice cold 1N HCl. Ethyl ether extractions 3×75 ml were dried (Na$_2$SO$_4$), and were evaporated to dryness. Purification was accomplished by either vacuum distillation or silica gel chromatography (1:4 ethyl ether:hexane).

69 percent yield. $^1$H NMR (CDCl$_3$) δ 0.95 (t, 3H); 1.70 (m, 2H); 2.54 (t, 2H); 3.23 (s, 1H). $^1$H NMR are consistent with literature values. Lockhart et al., *J. Am. Chem. Soc.*, 103:4082 (1981).

C. Synthesis of Methyl-4-oxo-5-hexynoate (Compound 38)

The following were combined in a dry flask under nitrogen at zero degrees C; 23 mmole bis(trimethylsilyl)acetylene, 23 mmole of an acid chloride and 80 ml dichloromethane. 3.07 grams of aluminum trichloride were added over 35 minutes under nitrogen at zero degrees C. The reaction was stirred overnight (about 18 hours) and permitted to warm to room temperature. The excess aluminum trichloride was destroyed by addition of 100 ml 1N HCl followed by extraction with 3×100 ml ethyl ether.

The dried organic layers (Na$_2$SO$_4$) were evaporated and the residue was purified by vacuum distillation or silica gel chromatography (1:9 ethyl ether:hexane). The trimethyl silyl group was removed by adding 15 ml 0.1M borax to a solution of methyl-4-oxo-5-hexynoate (1 g) in 80 ml methanol. The solution was kept at room temperature for 15 minutes and quenched with 75 ml ice cold 1N HCl. Ethyl ether extractions 3×75 ml were dried (Na$_2$SO$_4$), and were evaporated to dryness. Purification was accomplished by either vacuum distillation or silica gel chromatography (1:4 ethyl ether:hexane).

38 Percent yield. $^1$H NMR (CDCl$_3$) δ 2.64 (t, 2H); 2.91 (t, 2H); 3.28 (s, 1H); 3.68 (s, 3H). $^1$H NMR data are the same as reported previously. Kornilov et al., *Org. Khim.*, 24: 1343 (1988).

Although the present invention has now been described in terms of certain preferred embodiments, and exemplified with respect thereto, one skilled in the art will readily appreciate that various modifications, changes, omissions and substitutions can be made without departing from the spirit thereof.

We claim:

1. A process of making an R-configured alcohol comprising the steps of
   (a) forming a reaction mixture by admixing in a liquid medium (i) NADH, (ii) a catalytic amount of a PED alcohol dehydrogenase from *Pseudomonas sp.* ATCC No. 49794 and (iii) a carbonyl substrate of the formula I:

$$R\text{—}CO\text{—}R^1 \qquad I$$

wherein R is selected from the group consisting of hydrogen, C$_1$-C$_6$ alkyl, C$_1$-C$_6$ haloalkyl, C$_1$-C$_6$ acyl, C$_1$-C$_6$ alkoxy carbonyl, C$_1$-C$_6$ alkene and C$_1$-C$_6$ azaalkyl;
   R$^1$ is selected from the group consisting of phenyl, benzoyl, pyridyl, C$_1$-C$_3$ alkylenephenyl, C$_2$-C$_3$ oxaalkylenephenyl, C$_1$-C$_6$ alkoxy carbonyl, C$_1$-C$_6$ alkenyl, C$_1$-C$_6$ alkyl, C$_1$-C$_6$ haloalkyl, C$_1$-C$_6$ oxoalkyl, C$_1$-C$_6$ halo oxoalkyl, C$_1$-C$_3$ alkyl C$_1$-C$_3$ alkylenecarboxylate, C$_2$-C$_3$ alkynyl, C$_1$-C$_6$ hydroxy alkyl, and C$_1$-C$_6$ thiaalkyl, or R and R$^1$ together form a 5–7-membered ring that is free from unsaturation except for the carbonyl of formula I; and
   said carbonyl substrate has an overall chain length of three to about nine carbon atoms; and
   (b) maintaining the reaction mixture under biological reaction conditions and for a time period sufficient to reduce the carbonyl substrate and form the R-configured alcohol.

2. The process according to claim 1 further comprising the step of recovering the formed R-configured alcohol.

3. A process of making an R-configured alcohol with the regeneration of NADH comprising the steps of
   (a) forming a reaction mixture by admixing in a liquid medium (i) a catalytic amount of NAD, (ii) a catalytic amount of a PED alcohol dehydrogenase from *Pseudomonas sp.* ATCC No. 49794, (iii) a cofactor substrate and (iv) a carbonyl substrate of the formula I:

$$R\text{—}CO\text{—}R^1 \qquad I$$

wherein R is selected from the group consisting of hydrogen, C$_1$-C$_6$ alkyl, C$_1$-C$_6$ haloalkyl, C$_1$-C$_6$ acyl, C$_1$-C$_6$ alkoxy carbonyl, C$_1$-C$_6$ alkene and C$_1$-C$_6$ azaalkyl;
   R$^1$ is selected from the group consisting of phenyl, benzoyl, pyridyl, C$_1$-C$_3$ alkylenephenyl, C$_2$-C$_3$ oxaalkylenephenyl, C$_1$-C$_6$ alkoxy carbonyl, C$_1$-C$_6$ alkenyl, C$_1$-C$_6$ alkyl, C$_1$-C$_6$ haloalkyl, C$_1$-C$_6$ oxoalkyl, C$_1$-C$_6$ halo oxoalkyl, C$_1$-C$_3$ alkyl C$_1$-C$_3$ alkylenecarboxylate, C$_2$-C$_3$ alkynyl, C$_1$-C$_6$ hydroxy alkyl and C$_1$-C$_6$ thiaalkyl, or R and R$^1$ together form a 5–7-membered ring that is free from unsaturation except for the carbonyl of formula I; and
   said carbonyl substrate has an overall chain length of three to about nine carbon atoms; and
   (b) maintaining said reaction mixture under biological reaction conditions and for a time period sufficient to reduce said carbonyl substrate and form said R-configured alcohol.

4. The process according to claim 3 wherein the cofactor substrate is 2-propanol.

5. The process according to claim 4 wherein the 2-propanol is present in a concentration of 5 to about 10 volume percent.

6. The process according to claim 3 wherein the liquid medium contains a water immiscible non-reactive organic solvent for the carbonyl substrate.

7. The process according to claim 3 wherein R is C$_1$-C$_6$ alkyl, and R$^1$ is selected from the group consisting of phenyl, benzoyl, C$_1$-C$_6$ alkyl, C$_1$-C$_6$ oxoalkyl, C$_1$-C$_6$ halooxoalkyl, and C$_1$-C$_3$ alkyl C$_1$-C$_3$ alkylenecarboxylate.

8. A process of transferring a hydride ion to the pro-R face of NAD comprising the steps of
   (a) forming a reaction mixture by admixing in a liquid medium (i) said NAD, (ii) a catalytic amount of a PED alcohol dehydrogenase from *Pseudomonas sp.* ATCC No. 49794 and (iii) an R-configured alcohol of the formula Ia:

$$R\text{—}R^2COH\text{—}R^1 \qquad Ia$$

wherein R is selected from the group consisting of hydrogen, $C_1$–$C_6$ alkyl, $C_1$–$C_6$ haloalkyl, $C_1$–$C_6$ acyl, $C_1$–$C_6$ alkoxy carbonyl, $C_1$–$C_6$ alkene and $C_1$–$C_6$ azaalkyl;

$R^1$ is selected from the group consisting of phenyl, benzoyl, pyridyl, $C_1$–$C_3$ alkylenephenyl, $C_2$–$C_3$ oxoalkylenephenyl, $C_1$–$C_6$ alkoxy carbonyl, $C_1$–$C_6$ alkenyl, $C_1$–$C_6$ alkyl, $C_1$–$C_6$ haloalkyl, $C_1$–$C_6$ oxoalkyl, $C_1$–$C_6$ halo oxoalkyl, $C_1$–$C_3$ alkyl $C_1$–$C_3$ alkylenecarboxylate, $C_2$–$C_3$ alkynyl, $C_1$–$C_6$ hydroxy alkyl and $C_1$–$C_6$ thiaalkyl, or R and $R^1$ together form a 5–7-membered ring;

$R^2$ is hydrogen, deuterium or tritium;

said carbonyl substrate has an overall chain length of three to about nine carbon atoms; and (b) maintaining said reaction mixture under biological reaction conditions and for a time period sufficient to oxidize said R-configured alcohol and transfer said hydride ion to said pro-R face of said NAD to form NADH.

9. The process according to claim 8 wherein $R^2$ is hydrogen.

10. The process according to claim 8 further comprising the step of recovering the formed NADH.

11. The process according to claim 8 wherein the liquid medium contains a water immiscible, non-reactive organic solvent for the carbonyl substrate.

12. The process according to claim 8 wherein R is $C_1$–$C_6$ alkyl, and $R^1$ is selected from the group consisting of phenyl, benzoyl, $C_1$–$C_6$ alkyl, $C_1$–$C_6$ oxoalkyl, $C_1$–$C_6$ halooxoalkyl, and $C_1$–$C_3$ alkyl $C_1$–$C_3$ alkylenecarboxylate.

* * * * *